(12) United States Patent
Price-Jones et al.

(10) Patent No.: US 7,026,135 B2
(45) Date of Patent: Apr. 11, 2006

(54) BIOTIN-PEG-SUBSTRATE FOR A LIPASE ASSAY

(75) Inventors: Molly Jean Price-Jones, Cardiff (GB); David Martin James, Cardiff (GB); Anne Fowler, Cardiff (GB); Fritz Poulsen, Bagsvaerd (DK); Hans Tornqvist, Bagsvaerd (DK); Calvin Richard Hawes, Cardiff (GB)

(73) Assignee: Amersham Biosciences UK Limited, Amersham (GB)

( * ) Notice: Subject to any disclaimer, the term of this patent is extended or adjusted under 35 U.S.C. 154(b) by 457 days.

(21) Appl. No.: 10/239,806

(22) PCT Filed: Mar. 23, 2001

(86) PCT No.: PCT/GB01/01350

§ 371 (c)(1),
(2), (4) Date: Dec. 9, 2002

(87) PCT Pub. No.: WO01/73442

PCT Pub. Date: Oct. 4, 2001

(65) Prior Publication Data

US 2004/0014133 A1    Jan. 22, 2004

(30) Foreign Application Priority Data

Mar. 29, 2000    (GB) .................................. 0007465

(51) Int. Cl.
*C12Q 1/44* (2006.01)
*G01N 33/53* (2006.01)
*C08L 91/00* (2006.01)

(52) U.S. Cl. .................. 435/19; 435/7.5; 435/7.72; 524/313

(58) Field of Classification Search ............... 435/4, 435/7.4, 7.5, 7.72, 19, 198; 524/311, 313
See application file for complete search history.

(56) References Cited

FOREIGN PATENT DOCUMENTS

| WO | WO 91/08489 | 6/1991 |
| WO | WO 99/02186 | 1/1999 |

OTHER PUBLICATIONS

M. Duque, et al. "New fluorogenic triacylglycerol analogs as substrates for the determination and chiral discrimination of lipase activities" Journal of Lipid Research vol. 37, No. 4, 1996 pp. 868-876.
P. Nilsson-Ehle, et al. "A Stable Radioactive Substrate Emulsion for Assay of Lipo Protein Lipase" Journal of Lipid Research vol. 17, No. 5, 1976 pp. 536-541.

*Primary Examiner*—Jean C. Witz
*Assistant Examiner*—Susan Hanley
(74) *Attorney, Agent, or Firm*—Royal N. Ronning, Jr.; Yonggang Ji (57) ABSTRACT

Disclosed is a compound of Formula (I), wherein: L is a linking agent; B is a binding agent; X is an atom or group suitable for attaching L to the glycerol chain; and R is a straight chain saturated or unsaturated alkyl group having from 8 to 30 carbon atoms, substituted with M' or M" wherein at least one of M' and/or M" is a detectable label. The compound can be used as a lipase substrate in a solid phase-based assay system, such as a scintillation proximity assay, to detect lipase enzyme activity.

23 Claims, 5 Drawing Sheets

FIGURE 1

Reaction Scheme 1

BIOTIN-PEG-SUBSTRATE FOR A LIPASE ASSAY

The present invention describes a novel substrate for use in an assay for lipase enzyme activity. In particular, this novel substrate can be labelled and used in a homogeneous assay.

INTRODUCTION

Lipases are enzymes that catalyse the hydrolysis of triacylglycerols in the first step in recovering stored fatty acids for energy production. The sequence of hydrolysis from the three positions on glycerol depends on the specificity of the particular lipase involved.

Lipase enzyme activity is an important function and its strict regulation is necessary to ensure healthy metabolism. For example, lipases in adipose tissue are key enzymes for the release of major energy stores. Their activity is under hormonal control to ensure that triacylglycerol hydrolysis is balanced with the process of triacyglycerol synthesis to assure adequate energy stores and yet avoid levels of fatty acids becoming so high as to cause adverse effects.

One example of a lipase is Hormone Sensitive Lipase (HSL). This enzyme catalyses the rate-limiting step in lipolysis and utilisation of triacylglycerol stocks such as those found in adipose tissue and skeletal muscle. It is a cytosolic neutral lipase and its triacylglycerol substrate is hydrophobic. The enzyme is activated in insulin deficiency and/or insulin resistance causing depletion of lipid stocks in diabetes sufferers. Inhibition of the enzyme, therefore, is important in the management of diabetes.

Imbalances in the activity of lipases have also been linked to other clinical disorders including obesity and atherosclerotic vascular disease. In view of the importance of lipase activity in disorders such as these, it is necessary to have assays which are suitable for measuring enzyme activity. Such assays could provide a useful diagnosis for assessing the status of lipase activity-related disorders. In addition, assays that would be suitable for assessing the effectiveness of any compounds that may have the potential to modify (either to inhibit or enhance) enzyme activity are required.

Recent developments in genomics and combinatorial chemistry have generated large numbers of new drug targets and new compounds. In consequence, advances in drug discovery have focused on high throughput screening (HTS) technologies and miniaturisation. These technologies aim to screen large numbers of either candidate drug targets or new compounds to uncover new leads in a short time (High-throughput screening for drug discovery, James R. Broach and Jeremy Thorner. Nature Vol. 384, Supp, 7 November 1996, 14–16.). Key to the success of such HTS techniques is the development of assays which can be adapted into a miniaturised format and which have only a minimum number of steps in order to facilitate an automated screening process.

As substrates for lipases are generally hydrophobic in nature, current methods for measuring lipase enzyme activity typically involve a large number of processing steps including organic phase extraction.

For example, a typical current method for determining the activity of a lipase, such as Hormone Sensitive Lipase (HSL), would involve a substrate such as triacylglycerol, cholesteryl ester or diacylglycerol. The triacylglycerol substrate would, typically be radiolabelled e.g. by a 3H label. Prior to adding the substrate to the enzyme, a substrate emulsion would be formed by, for example, sonicating or vortexing a solution of the substrate in a buffer solution (for example 100 mM potassium phosphate at pH 7.0) containing 0.05% BSA or an emulsion stabiliser such as phospholipids. The substrate/enzyme mixture would then be incubated at 37° C. for 60 minutes after which reactions would be stopped by the addition of a stop solution (such as chloroform:methanol:heptane (25:23:18)). In order to determine enzyme activity on the substrate, it would be necessary to separate the products of the enzyme reaction from the labelled substrate by extracting the organic phase of the reaction solution. This would be achieved by vortexing and centrifuging the tubes containing the reaction solution and taking aliquots of the upper phase for liquid scintillation counting. Results would be expressed in nmol of fatty acid released/mg protein (see for example, Rapid assay for hormone-sensitive lipase activity of adipose tissue. H. Tornquist, L. Krabisch and P. Belfrage. Journal of Lipid Research,1972,13,424–426).

Such a multi-step procedure, involving vortexing and centrifugation, would be difficult to automate and inconvenient to perform on a large number of samples simultaneously. Accordingly, to date, no HTS techniques have been made available for screening for lipase enzyme activity or for compounds which may act as enhancers or inhibitors of this activity.

Recently, assays based on homogeneous techniques have been developed and these are readily adaptable to HTS. Generally, homogeneous assays involve detection via a solid phase binding step. One example of such an assay is the Scintillation Proximity Assay (SPA) (Scintillation proximity assay—a versatile high throughput screening technology. Cook, N. D.; *Drug Discovery Today,* 1:287–294 (1996)). This assay involves solid phase binding to microspheres or "beads" that contain a scintillant. If SPA beads are coated, for example, with a receptor and incubated with a $^3$H-labelled ligand, any ligand which binds to the receptor will be brought in close proximity to the bead such that its radiolabel excites the scintillant causing the emission of a light signal. SPA results can be read in 96 and 384 well plates using standard microplate scintillation counters or in 384 and higher density well plates using LEADseeker™ Homogeneous Imaging System (Imaging Proximity Assays—The LEADseeker Homogeneous Imaging System, A. Fowler, M. Harvey, A. Cox, B. Jessop, M. Looker, I. Davis, J. Morris, A. Santos, J. Turner and M. Price-Jones. Genetic Engineering News, Volume 18, Number 20, Nov. 15, 1998). The LEADseeker™ system features a CCD camera allowing imaging of high density microtitre plates in a single pass.

However, in order to adapt any assay which depends on solid phase binding, such as SPA, to an assay for lipase enzyme activity, it would be necessary to modify the lipase substrate to render it capable of binding to a surface. Due to their hydrophobic nature, lipase substrates are not readily amenable to the modifications, such as biotinylation or other labelling, that would be required for solid phase binding. Moreover, in view of the high specificity of lipase enzymes for hydrophobic substrates, there would be no guarantee that a lipase substrate modified to be suitable for solid phase detection would still be recognised by the enzyme.

In the present invention, a lipase substrate has been modified so that it can be bound to a solid surface, such as streptavidin-coated SPA beads, and is shown to act as an effective lipase substrate in an assay for lipase enzyme activity. In a particular embodiment, a substrate has been designed with an amino group in the sn-2 position and oleic acid (18:1) in the sn-1 and sn-3 positions of the triacylglycerol; the oleic acid can be labelled by reductive tritiation. It has been found that this substrate can be biotinylated by incorporating a biotin group on a PEG spacer arm to generate a novel modified lipase substrate. Lipase activity removes the radiolabelled portion which, in an SPA, results in a decreased light signal from the SPA beads.

In accordance with a first aspect of the invention there is provided a compound of Formula I:

FORMULA I wherein L is a linking agent comprising a water-soluble molecule;
B is a binding agent;
X is an atom or group suitable for attaching L to the glycerol chain; and
R is a straight chain saturated or unsaturated alkyl group having from 8 to 30 carbon atoms, substituted with M' or M" wherein at least one of M' and M" is a detectable label.

The linking agent, L, is a group which links a binding agent, B, to a triacyglycerol in such a way that the lipase substrate can be attached to a solid surface and yet still retain its biological activity. The linking agent is a water-soluble molecule which can be nontoxic and/or inert. In a preferred embodiment of the first aspect, the linking agent, L, comprises a water-soluble compound selected from the compounds polyethylene glycol (PEG) and polyvinylpyrrolidone (PVP). Each of these compounds can exist as a polymer of a number of repeating units. Suitably, where L comprises PEG, the size of the PEG polymer is between 6–100 repeating units.

In another embodiment of the first aspect of the invention, binding agent, B, is capable of binding to a solid phase such as the walls or base of wells in a plate, for example a microtitre plate, or to the surface of a bead such as an SPA bead. Binding of the binding agent, B, to a solid surface can be direct or indirect. For example, a compound can be bound to a solid phase by indirect means such as by coating the solid surface with one member of a specific binding pair and attaching the other member to the compound of Formula I. Attachment can be by non-covalent or covalent means.

In a preferred embodiment, binding agent, B, comprises one member of a specific binding pair, said specific binding pair being preferably selected from biotin:avidin or streptavidin, antibody: antigen or protein A, receptor:ligand, nucleic acid:nucleic acid (e.g.DNA:DNA), wheatgerm agglutinin (WGA): N-acetyl β glucosamine residues or glycoproteins, glutathione:GST (glutathione-S-tranferase) and copper:histidine tag. Other suitable specific binding pairs would be known to those skilled in the art. Alternatively, binding can be achieved by electrostatic interaction, for example by creating a positively charged species on B which is bound to a negatively charged species on the solid phase. A positive charge could be generated, for example, using a quaternised amine.

In a particularly preferred embodiment of the first aspect of the invention, the binding agent, B, is biotin. This would render the compound of Formula I capable of binding to an avidin or streptavidin-coated solid phase.

X is an atom or group which enables the linking agent, L, to bind to the carbon backbone (i.e. the glycerol chain) of the compound set out in Formula I and is chosen according to the reactive groups present on the linking agent which are available for attachment. Thus, in one embodiment, if the linking agent, L, has a reactive group NHS then X would comprise NH. In one example, the NHS group may be attached to the linking agent through an ester linkage in which case group X may comprise O=C—NH. In another embodiment, if the linking agent, L, has maleimide as a reactive group then X would comprise S. Suitable coupling mechanisms involving NH, S or O atoms would be recognised by someone skilled in the art.

Different lipases have specificity for triacylglycerols having fatty acids with different length carbon chains; these carbon chains are typically between 8–30 carbon atoms and can be either saturated or unsaturated. Accordingly, in the compound of Formula I, R is a straight chain saturated or unsaturated alkyl group having from 8 and 30 carbon atoms. Stored fatty acids, such as those which form the substrates for some lipases, generally have between 14 and 18 carbon atoms in the carbon chain. Accordingly, in another embodiment of the first aspect of the invention there is provided a compound of formula I wherein R has 14, 16 or 18, and preferably 18 carbon atoms.

R is substituted with M' or M" wherein at least one of groups M' and M" is a detectable label. Where either of M' or M" is not a detectable label it would, preferably, be H. Suitable detectable labels can be radiolabels, fluorescence labels or other labels (including luminescent molecules for example). In one embodiment, at least one of M' and M" is a radiolabel such as $^3$H, $^{125}$I or $^{14}$C, or any other labels which may be suitable for use in a scintillant detection system such as SPA or other solid phase based assay systems (for example Cytostar-T™ scintillating microplates (Amersham Pharmacia Biotech) or Flashplates™ (NEN)). In such systems, when the detectable label is close to a solid surface, scintillation events can be detected but when lipase activity occurs the label is released with the fatty acid and the scintillant signal decreases. In a particularly preferred embodiment, M' and/or M" is $^3$H. It is understood by those skilled in the art that migration of the fatty acid chains occurs between the sn-1, sn-2 and sn-3 positions of the carbon backbone of a triacylglycerol.

In another preferred embodiment of the first aspect of the invention, at least one of M' and M" is a fluorophore. Suitable fluorophores include, for example, those based on fluorescein and its derivatives (Handbook of Fluorescent Probes and Research Chemicals, Molecular Probes, 6$^{th}$ Edition, 1996 and cyanine dye molecules (Cy dyes).

In a further embodiment of the first aspect, M' and M" could be chosen to enable a compound of Formula I to be used in a Fluorescence Resonance Energy Transfer (FRET) assay. The principal of FRET was described in U.S. Pat. No. 4,996,143 and, more recently, in PCT/GB99/01746 (publication number WO99/64519). Briefly, FRET assays depend on an interaction between two fluorophores, a donor fluorophore and an acceptor fluorophore. When the donor and acceptor molecules are in close enough proximity, the fluorescence of the donor molecule is transferred to the acceptor molecule with a resultant decrease in the lifetime and a quenching of fluorescence of the donor species and a concomitant increase in the fluorescence intensity of the acceptor species. When the two molecules are separated, the fluorescence of the donor molecule is restored and the fluorescence intensity of the acceptor species decreases. The use of FRET labels in biological systems is well known. The principle has been used in the detection of binding events or cleavage reactions in assays which employ FRET.

Suitable acceptor/donor pairs for use in a FRET assay are described in Handbook of Fluorescent Probes and Research Chemicals, Molecular Probes. To adapt a FRET assay for use in a lipase substrate-enzyme assay, one of the acceptor or donor would be contained in the bead or other solid phase, the other would be linked onto the substrate of Formula I in either/both the M' and M" position(s) such that one partner of the acceptor/donor pair was on the substrate and the other in the bead. The donor and acceptor molecules would be held in close proximity when the substrate is bound to the bead. Upon lipase enzyme activity on the substrate, cleavage in the sn-1 and sn-3 positions will cause the donor and acceptor molecules to be separated thus restoring the fluorescence of the donor molecule with a concomitant decrease in the fluorescence intensity of the acceptor species.

In one format of the FRET principle, a fluorescent agent is caused to be in close proximity with a "quencher" molecule such that the energy from the excited donor fluorophore is transferred to the quencher and dissipated as heat rather than fluorescence energy. In this case, residual fluorescence is minimised when the two components of the donor-quencher pair are in close proximity and a large change in signal can be obtained when they are separated.

Cyanine dyes suitable for use as acceptor or "quencher" molecules in a FRET assay have been developed (see PCT/GB99/01746) by making certain modifications to cyanine dyes through introduction of chemical groups which have the effect of diminishing or abolishing the fluorescence of the molecule. Such quenched Cy dyes are referred to as Cy-Q dyes or "dark cyanine dyes".

Accordingly, in another embodiment of the invention, the fluorophore attached at one or both of M' and M" could be a "quencher" or "dark cyanine dye" molecule such as Cy-Q and the streptavidin-coated bead could contain a normal fluorescent fluorophore. When the substrate is bound to the bead, the fluorescence of the fluorophore in the bead will be quenched. When the lipase enzyme activity causes one or both of the sn-1 and sn-3 fatty acid chains to be cleaved from the substrate, the "quencher" fluorophores will be disassociated from the bead and thus the fluorescence of the fluorophore within the bead will be restored. Accordingly, lipase enzyme activity would be detected by measuring an increase in fluorescence.

In an alternative embodiment, the normal fluorescent fluorophore could be attached at one or both of M' and M" and the "quencher" molecule could be contained in the streptavidin-coated bead.

In a second aspect of the invention, there is provided a method for preparing a compound according to any embodiment of the first aspect of the invention.

In one embodiment of the second aspect, the method comprises the steps of:
 a) performing a reaction to add a detectable label, M' or M", to a triacylglycerol; and
 b) attaching a binding agent, B, to said triacylglycerol molecule through a linking agent, L.

In another embodiment, step a) comprises a tritiation reaction, preferably adding $^3$H to the acyl carbon chains in the sn-1 and/or sn-3 positions.

In a further embodiment, B is attached to a triacylglycerol molecule via L wherein L is a PEG spacer arm. In a particularly preferred embodiment, step b) comprises reacting said triacylglycerol molecule with Biotin PEG NHS ester.

The compound of Formula I forms a substrate for a lipase. Lipases which can be assayed with a substrate of Formula I include lipases extracted from mammalian, yeast or bacterial cells (examples of lipases include those extracted from wheat germ, *Chromobacterium, Mucor, Pseudomonas, Candida*, lipoprotein lipase, hepatic and pancreatic lipases and Hormone Sensitive Lipase (HSL)). A composition can comprise a solution containing a lipase enzyme or a cell or cell extract. In principle, any type of cell can be used i.e. prokaryotic or eukaryotic (including bacterial, mammalian and plant cells). Where appropriate, a cell extract can be prepared from a cell, using standard methods known to those skilled in the art (Molecular Cloning, A Laboratory Manual $2^{nd}$ Edition, Cold Spring Harbour Laboratory Press 1989).

In a third aspect of the invention there is provided an assay for detecting lipase enzyme activity in a composition, said assay comprising incubating said composition in the presence of the compound of Formula I as claimed in any embodiment of the first aspect and measuring release of the detectable label, M' and/or M", from the compound as an indication of lipase activity.

The presence of binding agent, B, in the compound of Formula I makes it possible to use this enzyme substrate in a homogeneous assay which involves a solid phase binding step.

Accordingly, in a fourth aspect of the invention there is provided an assay for detecting lipase enzyme activity in a composition comprising:
 a) mixing said composition with a compound of Formula I as claimed in any embodiment of the first aspect;
 b) incubating under conditions to promote lipase enzyme activity,
 c) adding a solid phase under conditions to promote binding of the compound to the solid phase; and
 d) detecting the amount of M' and/or M" on the solid phase as an indication of lipase enzyme activity.

In a fifth aspect of the invention there is provided an assay for detecting lipase enzyme activity in a composition comprising:
 a) incubating the compound of Formula I as claimed in any embodiment of the first aspect with a solid phase under conditions to promote solid phase binding;
 b) adding said composition to said solid phase-bound compound;
 c) incubating under conditions to promote lipase enzyme activity;
 e) detecting the amount of M' and/or M" on the solid phase as an indication of lipase enzyme activity.

In one embodiment of the fourth or fifth aspects binding of the compound to the solid phase brings the compound into proximity with a scintillant and detection of M' and/or M" on the solid phase is by counting scintillation events i.e. "scintillation counting".

In another embodiment of the fourth or fifth aspects the solid phase is the surface of an SPA bead, preferably a streptavidin coated yttrium silicate (YSi) or PVT (poly (vinyl toluene)) SPA bead. Other suitable beads include or YOx (yttrium Oxide) (Amersham Pharmacia Biotech) or polystyrene (PST) beads.

In a further embodiment there is provided an assay wherein the solid phase is a surface of a plate such as a microtitre plate, preferably a Cytostar™ plate (Amersham Pharmacia Biotech) or Flashplates™ (NEN).

Enzyme assays can, for example, be run in 96 SPA or 384 well LEADseeker™ format and will be suitable for use in screening. The LEADseeker™ system features a CCD camera allowing imaging of high density microtitre plates in a single pass. This can be used for reading assays in radioactive, fluorescent and luminescent formats.

The lipase enzyme substrate of Formula I can be used in an assay for identifying the presence in a composition of a compound which can modify lipase enzyme activity. Accordingly, in a particularly preferred embodiment of any of the third, fourth or fifth aspects of the invention said composition comprises a lipase enzyme and a putative inhibitor or enhancer of lipase enzyme activity.

In one embodiment of any of the third, fourth or fifth aspects of the invention, the assay further comprises adding a stop solution to the reaction mixture prior to measuring M' or M".

In a sixth aspect of the invention there is provided a use of a compound of Formula I in accordance with any embodiment of the first aspect in an assay according to any embodiment of the third, fourth or fifth embodiments.

The present invention is further illustrated with reference to the following Figures and Examples in which.

EXAMPLE 1

Figure 1:
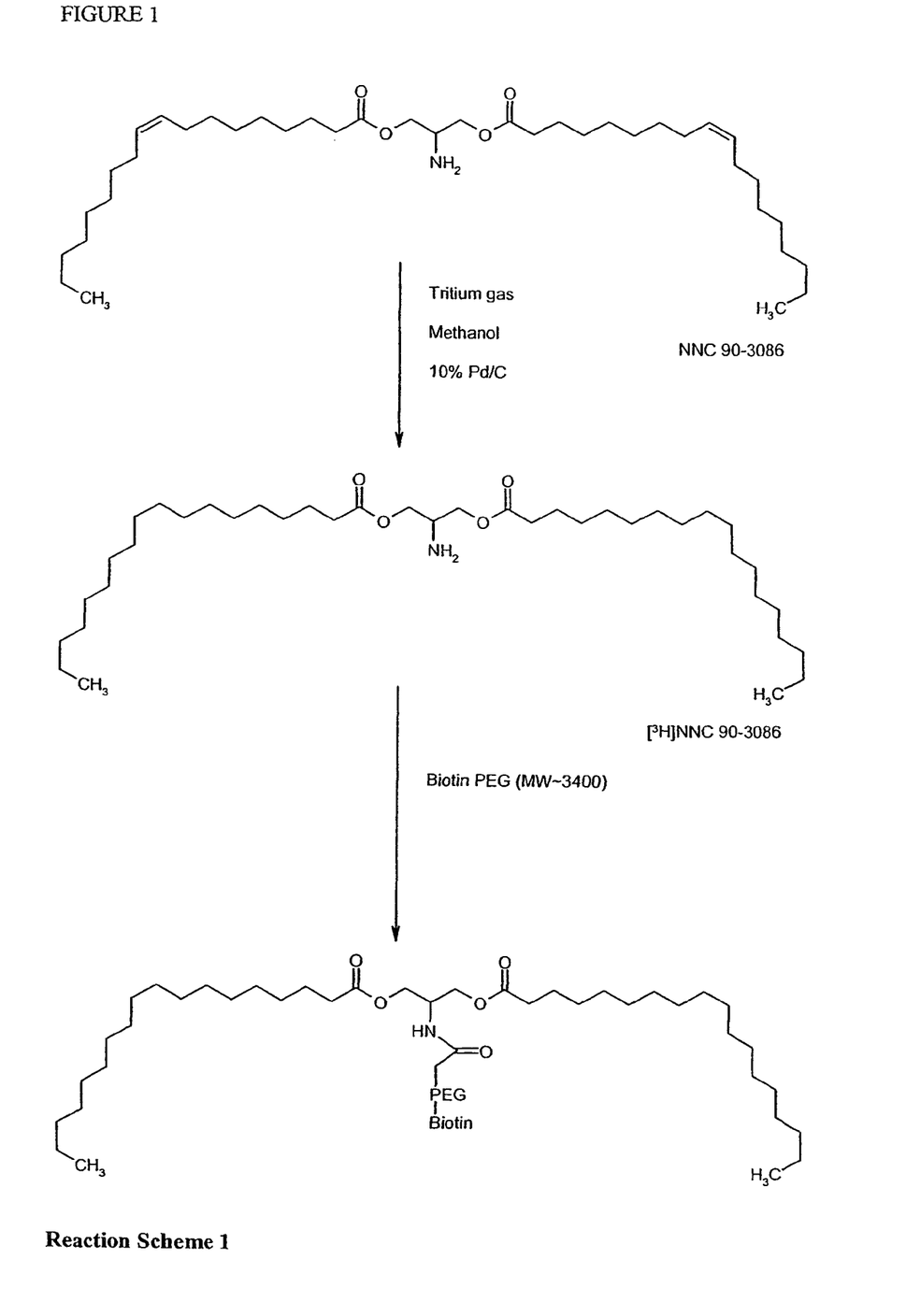
FIG. 1 shows a reaction Scheme 1 for preparation of HSL substrate.

A method for synthesising a lipase substrate for HSL is set out in Reaction Scheme 1 (see FIG. 1).

Briefly, a tritiation reaction was carried out as follows:

Approximately 25 mg of the hydrochloride salt of 9(Z)-octadec-9-enoic acid 2-amino-3-3((9Z)-octadec-9-enoyloxy)propyl ester (NNC 90-3086) was combined with 10% palladium on charcoal (25 mg) and methanol (1.5 ml) in a tritiation vessel and stirred under tritium gas (10 Ci) for 90 minutes. This gave a crude yield of tritiated product of approximately 3.3 Ci.

This crude material was purified by high performance liquid chromatography (HPLC) on a Progidy ODS column (Phenomenex) using a methanol:water:trifluroacetic acid (90:10:0.1) (buffer A) and methanol:trifluroacetic acid (100:0.1) (buffer B). A gradient of 0% B to 100% B was run over 30 minutes at 3 ml/min. The yield after purification was approximately 1.6 Ci.

The tritiated compound, [$^3$H]NNC 90-3086 (1.6 Ci, 2.5 ml), was then biotinylated by forming a dimethylformamide solution and adding it to a Biotin PEG NHS ester (from Shearwater Polymers, Inc.) (MW~3400, 57 mg) and diisopropylethylamine (100 μl). The reaction mixture was heated at 100° C. for 45 minutes.

The resultant product was partially purified on a short silica column eluting in dichloromethane:methanol (9:1) then purified by thin layer chromatography on a short silica gel eluting in 4 ml dichloromethane followed by 8 ml dichloromethoane:methanol (9:1).

Typically, the radiochemical purity of [$^3$H]HSL substrate achieved was >95% and the specific activity was ~100 Ci/mmol.

EXAMPLE 2

A Screening Assay for a Lipase Using Scintillation and Imaging Proximity Assay Technologies Method 96-well SPA format. Using an 'on bead' assay format, 180 nM lipase substrate (i.e. HSL substrate prepared by the method described in Example 1) was added to streptavidin coated yttrium silicate (YSi) beads (Amersham Pharmacia Biotech) at 5 mg/ml and 10% (v/v) Triton™ X-100 in the ratio of 1:3:2. Triton X-100 was added to prevent non-specific binding of the tritiated product to beads. Assays contained 20 μl substrate precoated SPA beads (6 nM lipase substrate, 50 μg beads, 0.67% (v/v) Triton X-100), 5 nM lipase and assay buffer (50 mM Hepes, pH 7.5, 1 mM dithioerythritol (DTE) and 0.001% (v/v) C13E12) in a volume of 100 μl. In 'no enzyme' controls, approximately 15000 SPA cpm were obtained. After incubation for 60 minutes at room temperature with agitation, assays were stopped by the addition of 100 μl 0.1M sodium citrate/citric acid, pH 4.0 and counted on a TopCount™ microplate scintillation counter (Packard Instruments Co., Meriden, Conn., USA).

384-well SPA and LEADseeker formats. 180 nM lipase substrate was added to streptavidin coated YSi beads at 10 mg/ml and 10% (v/v) Triton™ X-100 in the ratio of 2:3:1. Assays contained 101 μl substrate precoated streptavidin YSi SPA beads or streptavidin yttrium oxide (YOx) LEADseeker beads (Amersham Pharmacia Biotech) (24 nM lipase substrate, 50 μg beads, 0.67% (v/v) Triton X-100), 30 nM lipase and assay buffer in a volume of 25 μl. In 'no enzyme' controls, approximately 6000 SPA cpm and 600 IOD's (Integrated Optical Density) were obtained. After incubation for 60 minutes at room temperature with agitation, assays were stopped by the addition of 25 μl 0.1M sodium citrate/citric acid, pH 4.0 and counted on either on a TopCount microplate scintillation counter (Packard Instruments Co., Meriden, Conn., USA) or imaged on LEADseeker (Amersham Pharmacia Biotech).

Results

Figure 2:
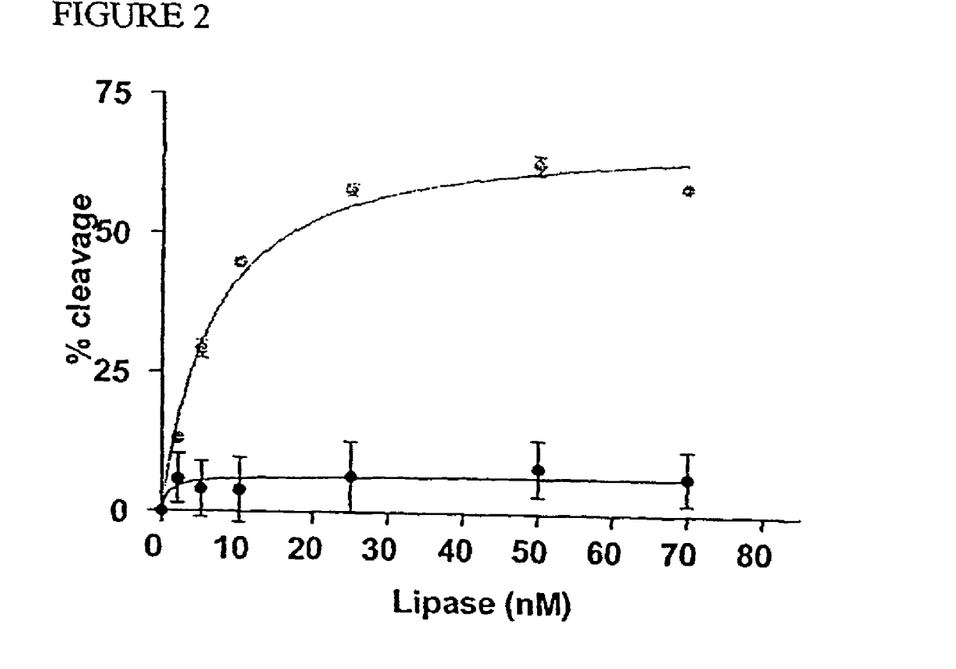
FIG. 2 shows the results of an enzyme titration comparing 'on' (○) and 'off' (●) bead assay formats.

Development of a lipase assay using a 96-well SPA assay format. Enzyme titrations were set up using 'on' and 'off' bead assay formats. In the 'off' bead format, the lipase substrate was not precoated onto SPA beads; instead the beads were added at the same time as the stop solution. Using an 'on' bead assay format resulted in a higher percentage of substrate cleavage than using an 'off' bead format and a more reproducible assay, as seen by the tighter error bars. It is thought that the binding of the substrate to the bead surface produced an artificial membrane environment necessary for optimal enzyme activity (FIG. 2). Each data point in this and subsequent figures is the mean (±SEM) of 3 replicates.

The maximum substrate cleavage obtained was approximately 60%. Due to the nature of the 'on' bead assay, it is unlikely that 100% substrate cleavage would be obtained since steric hindrance, caused by the presence of the bead, is likely to affect enzyme activity.

Figure 3:
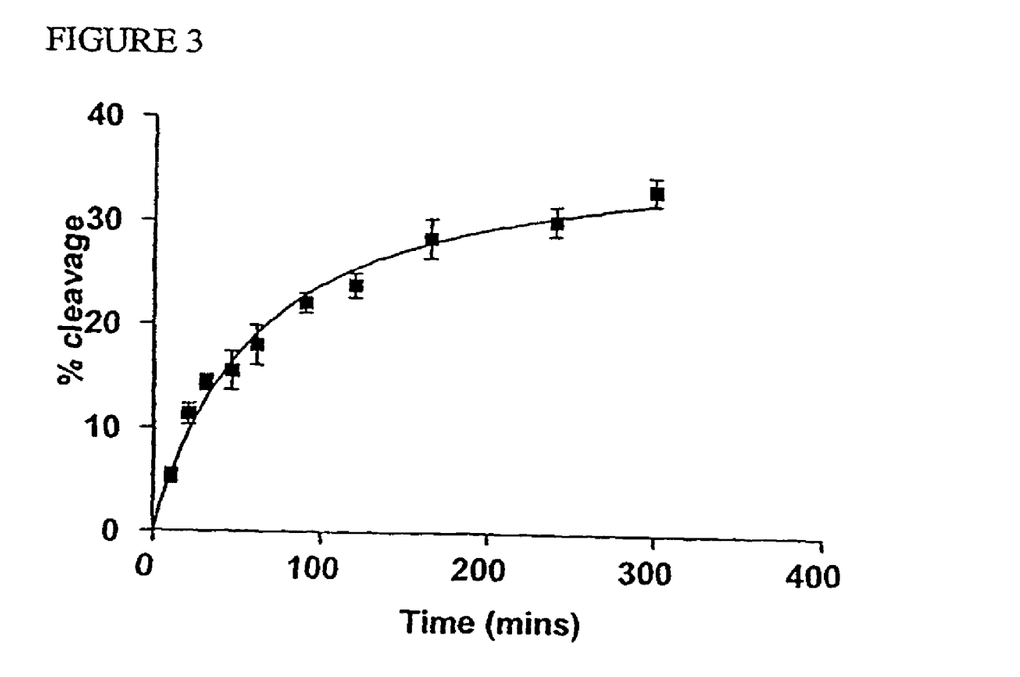
FIG. 3 shows the effect of time on substrate cleavage by 5 nM lipase.

Using the 'on' bead assay format, a time course was established using 5 nM lipase (FIG. 3).

Figure 4:
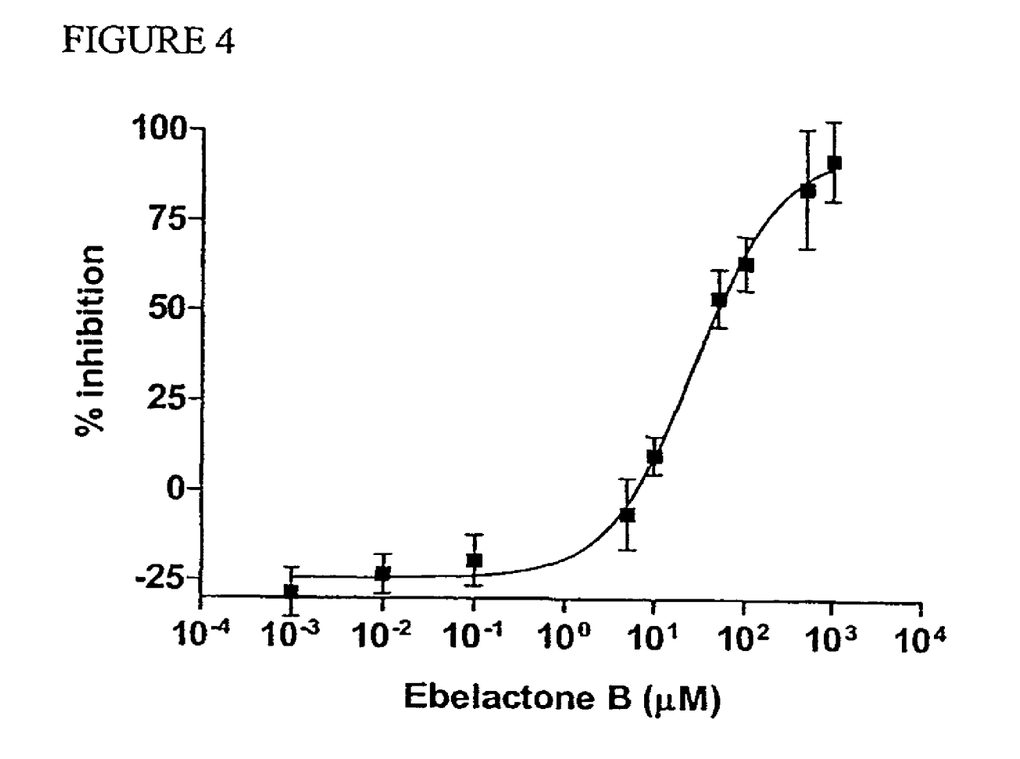
FIG. 4 shows inhibition of lipase activity by Ebelactone B.

Ebelactone B, a natural product from *Streptomyces aburaviensis*, is known to be an inhibitor of lipase activity (Nonaka, Y. et al, J. Enzyme Inhibition 10, pp 57–63 (1995)). Inhibition studies were carried out using Ebelactone B and an $IC_{50}$ value of 27.5 µM was obtained (FIG. 4). 5 nM lipase was used and assays were incubated at room temperature for 60 minutes.

Figure 5:
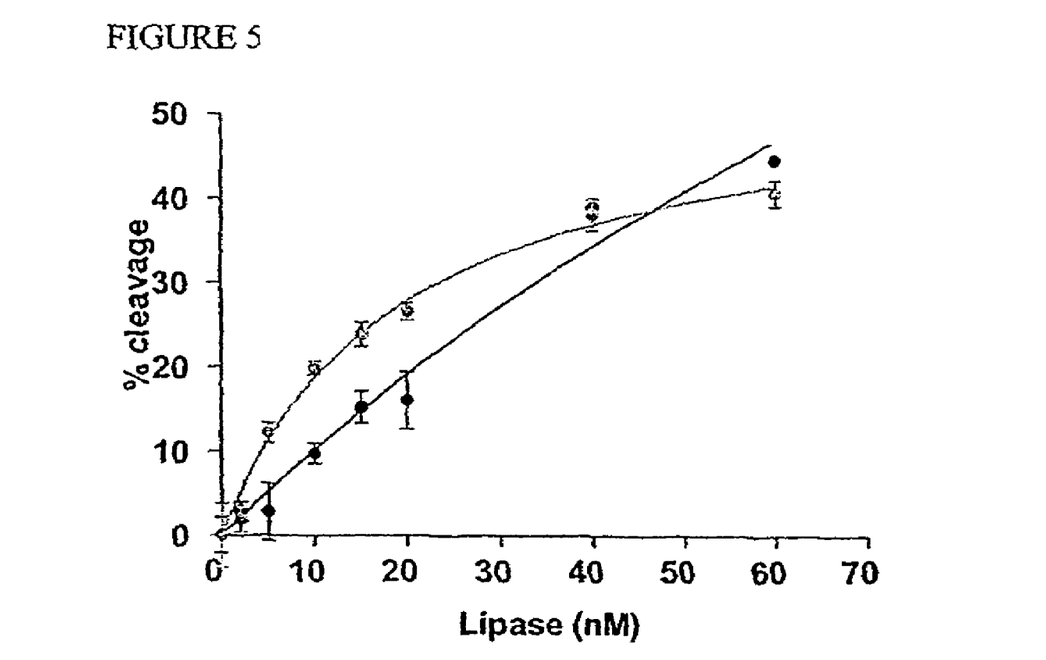
FIG. 5 shows the results of an enzyme titration comparing SPA (○) and LEADseeker (●) assay formats.

Miniaturization of the lipase assay to 384-well format using SPA and LEADseeker. Using a reduced assay volume an enzyme titration was performed with YSi SPA beads and YOx LEADseeker beads (FIG. 5). Different profiles were obtained using the two assay formats and this may be a result of how the substrate is presented on the surface of the two bead types.

Figure 6:
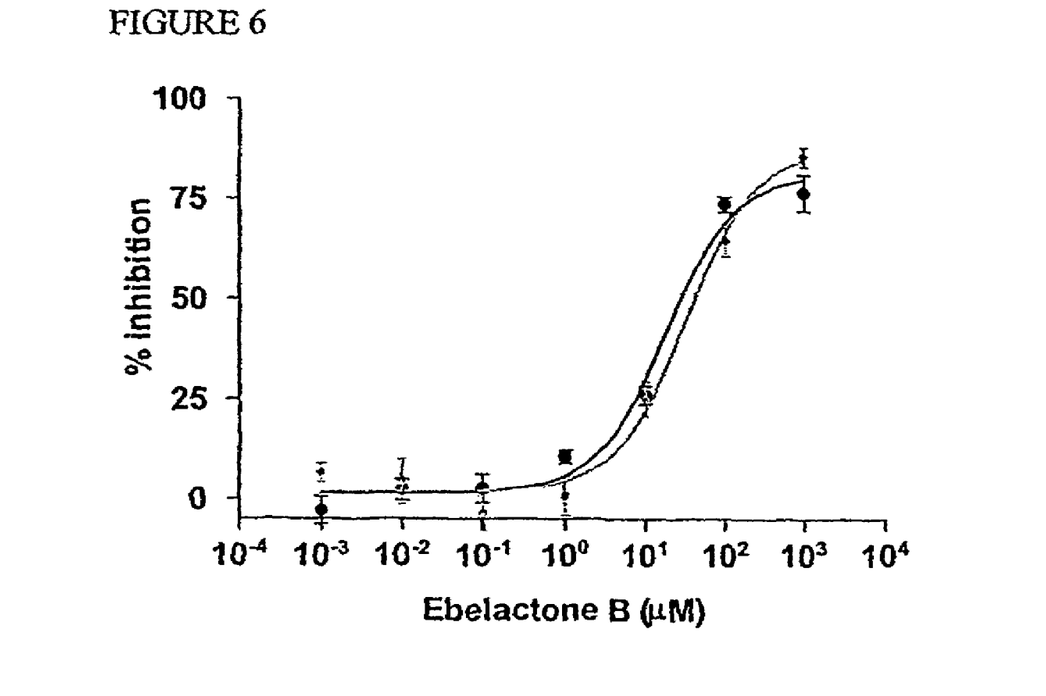
FIG. 6 shows inhibition of lipase activity by Ebelactone B detected using YSi SPA beads (○) and YOx LEADseeker beads (●).

Inhibition curves were obtained for the miniaturized assays using Ebelactone B and $IC_{50}$ values of 32.3 µM and 18.2 µM were determined using SPA and LEADseeker formats, respectively (FIG. 6). These values are comparable to the one calculated using the 96-well SPA assay format. 30 nM lipase was used and assays were incubated at room temperature for 60 minutes.

EXAMPLE 3

Cleavage of Lipase Substrate by Other Lipases

Figure 7:
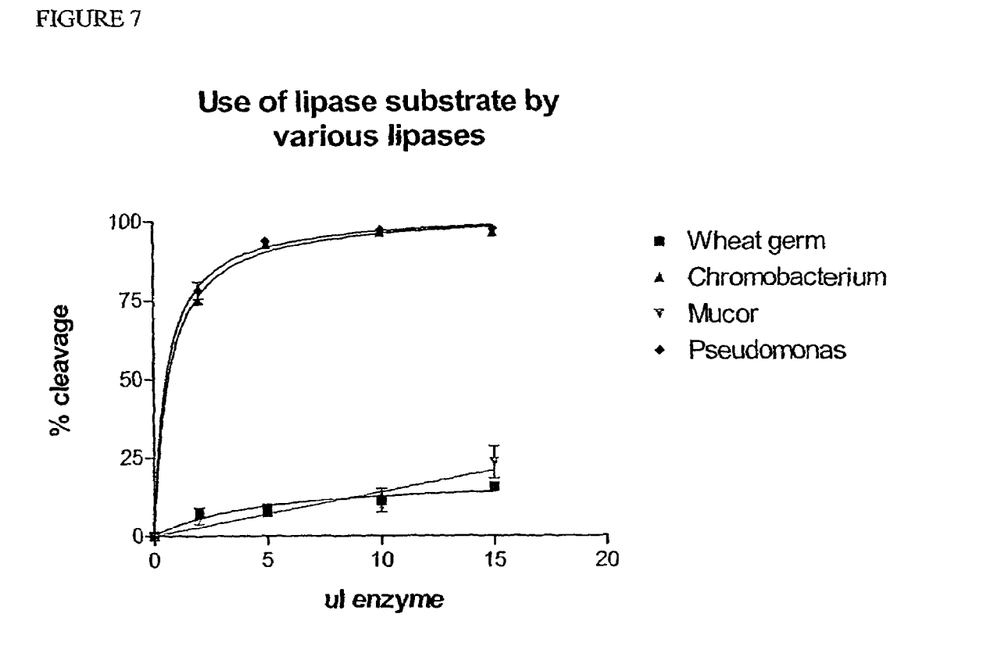
FIG. 7 demonstrates cleavage of HSL substrate by a range of lipases.

The standard assay format (as described in Example 2 above) was performed with lipase enzymes derived from number of different sources. The results are shown in FIG. 7.

EXAMPLE 4

Inhibition of HSL Activity by PMSF

The inhibition of HSL activity by PMSF was investigated using the standard assay format (as described above in Example 2) and 14.35 mM to 1.44 nM PMSF. Assays were incubated at room temperature for 60 minutes.

Figure 8:
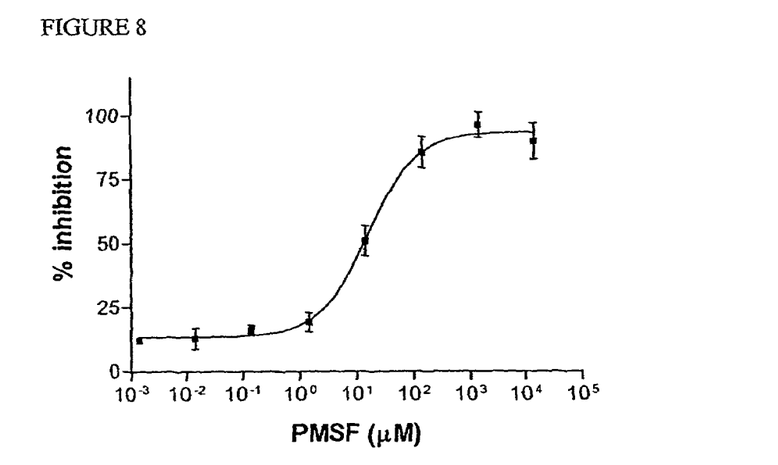
FIG. 8 shows inhibition of HSL by PMSF.

An $IC_{50}$ value of 16.3 µM was obtained. In similar experiments, $IC_{50}$ values of 4.8, 10.6 and 16.7 µM were obtained. Results are shown in FIG. 8.

What is claimed is:

1. A compound comprising Formula I:

FORMULA I wherein L is a linking agent including a water-soluble molecule;
B is a binding agent;
X is an atom or group suitable for attaching L to a glycerol chain; and
R is a straight chain saturated or unsaturated alkyl group having from 8 to 30 carbon atoms, substituted with M' or M" wherein at least one of M' and/or M" is a detectable label.

2. The compound of claim 1 wherein L includes a water-soluble molecule selected from PEG or PVP.

3. The compound of claim 1 wherein L includes 6–100 units of PEG.

4. The compound of claim 1 wherein B is capable of binding to a solid phase.

5. The compound of claim 1 wherein B includes one member of a specific binding pair.

6. The compound of claim 1 wherein B is biotin.

7. The compound of claim 1 wherein X is NH, O or S.

8. The compound of claim 1 wherein R has 14, 16 or 18 carbon atoms.

9. The compound of claim 1 wherein at least one of M' and M" is a radioactive label.

10. The compound of claim 1 wherein at least one of M' and M" is a fluorophore.

11. A method for preparing the compound of claim 1 comprising the steps of:
 a) reacting the sn-1 and/or sn-3 positions of a triacyglycerol with a detectable label, M' or M", to make a first modified triacylglycerol that is bonded to M' and/or M" at the sn-1 and/or sn-3 positions; and
 b) reacting said first modified triacylglcerol of step a) with a binding agent, B, through a linking agent, L, at the sn-2 position of said first modified triacylglycerol to make a second triacylglcerol that is bonded to M' and/or M" at the sn-1 and/or the sn-3 positions; and bonded to B though X-L at the sn-2 position.

12. The method of claim 11 wherein step a) includes a tritiation reaction, preferably adding $^3H$ in the sn-1 and/or sn-3 positions.

13. The method of claim 11, step b), wherein said first modified triacyglycerol molecule is reacted with an ester B-X-L, wherein B is biotin and L is NHS-PEG.

14. An assay for detecting lipase enzyme activity in a composition comprising incubating said composition in the presence of the compound of claim 1 and measuring release of the detectable label, M' and/or M", from the compound as an indication of lipase activity.

15. An assay for detecting lipase enzyme activity in a composition comprising:
 a) mixing said composition with the compound of claim 1 to make a mixture;
 b) incubating the mixture of step a) under conditions to promote lipase enzyme activity;
 c) adding a solid phase under conditions to promote binding of said compound in said incubated mixture; and
 d) detecting the amount of M' and/or M" on the solid phase as an indication of lipase enzyme activity.

16. An assay for detecting lipase enzyme activity in a composition comprising:
 a) incubating the compound of claim 1 with a solid phase under conditions to promote solid phase binding to make a solid phase-bound compound;
 b) adding said composition to said solid phase-bound compound of step a) to make a mixture;
 c) incubating said mixture of step b) under conditions to promote lipase enzyme activity; and
 d) detecting the amount of M' or M" on the solid phase as an indication of lipase enzyme activity.

17. The assay of claim 15 wherein binding to the solid phase brings the compound into proximity with a scintillant and detection of M' or M" on the solid phase is by measuring scintillation counts.

18. The assay of claim 15 wherein the solid phase is the surface of an SPA bead.

19. The assay of claim 15 wherein the solid phase is a surface of a plate.

20. The assay of claim 14 wherein said composition comprises a lipase enzyme and a putative inhibitor or enhancer of lipase enzyme activity.

21. The assay of claim 14 wherein a stop solution is added prior to detecting M' and/or M".

22. The compound of claim 5 wherein the specific binding pair is selected from the group consisting of biotin:avidin/streptavidin, antibody:antigen/protein A, nucleic acid:nucleic acid, receptor:ligand, WGA:N-acetyl β glucosamine, glutathione:GST (glutathione-S-transferase) and copper:histidine tag.

23. The assay of claim 19 wherein the plate is a microtitre plate.

* * * * *